United States Patent [19]

Feldman

[11] 4,192,204
[45] Mar. 11, 1980

[54] SOFT CONTACT LENS APPARATUS

[76] Inventor: Michael A. Feldman, 864 Glenridge Ave., North Woodmere, N.Y. 11581

[21] Appl. No.: 930,806

[22] Filed: Aug. 3, 1978

[51] Int. Cl.² .............................................. B25B 9/02
[52] U.S. Cl. .................................. 81/43; 294/1 CA; 294/99 R
[58] Field of Search ............... 81/43; 294/1 CA, 99 R

[56] References Cited
U.S. PATENT DOCUMENTS

| | | |
|---|---|---|
| 528,257 | 10/1894 | Murray . |
| 3,063,083 | 11/1962 | Obitts . |
| 3,115,360 | 12/1963 | Witkoff .................... 294/99 R |
| 3,628,824 | 12/1971 | Leuw et al. ................ 81/43 X |
| 3,675,962 | 7/1972 | Simpson ................... 294/99 R |
| 3,791,689 | 2/1974 | Boone et al. .............. 294/1 CA |
| 3,817,078 | 6/1974 | Reed et al. ................ 81/43 X |
| 3,971,270 | 7/1976 | Wallace ..................... 81/43 |
| 4,082,339 | 4/1978 | Ross ........................ 294/1 CA |

*Primary Examiner*—James G. Smith
*Attorney, Agent, or Firm*—Peter L. Berger

[57] ABSTRACT

A soft contact lens apparatus formed of a resilient material having a generally U-shape. A control portion forms the seat of the U-shape, while an intermediate fulcrum section operates to spread forwardly located finger and tip means as said control portion is squeezed together. When released, the material's resiliency allows the tips to return to their substantially closed position. This return movement is used to pinch the soft contact lens from the eye without injury or damage to the eye or lens since the tips are made of soft yet firm material, and the amount of force is slight and predetermined by the natural resiliency of the material. The apparatus may also be used to insert the lens.

11 Claims, 3 Drawing Figures

SOFT CONTACT LENS APPARATUS

BACKGROUND OF THE INVENTION

The present invention relates to a novel soft contact lens device used for insertion and removal of the lens.

Contact lenses can be made to correct most visual conditions correctable by regular eyeglasses. Moreover, contact lenses are not readily visible and provide the user with a wider field of vision than do eyeglasses.

The first contact lenses were of the "hard" variety, that is to say, they are lathe cut and polished or are molded of a relatively rigid material, usually methylmethacrylate, and formed by heat and pressure to the exact shape of the wearer's eye. The user must learn to wear them over a period of time. Many persons have experienced difficulty in wearing hard contact lenses.

A recent innovation has beeen the "soft" contact lens constructed of flexible and liquid absorbent material such as 2-hydroxethyl methacrylate. Although very comfortable to wear, the soft contact lens has some problems, including the difficulty of removal.

Generally, soft contact lenses are removed by the wearer moving the contact lens off the cornea onto the sclera and pinching the soft contact between his fingertips, thereby removing the contact lens from the eye. Unfortunately, some people have difficulty in removing the contact lens because of their difficulty in placing their fingers on the cornea, while others have long or sharp fingernails and still others are generally clumsy having large fingers.

As discussed above, hard contact lenses are easily removed by a scissoring action of the eyelids or by suction cup type of removal devices. Such a scissoring action is inappropriate for soft contact lenses, and a suction device does not effectively work because of the relative potential damage which can be done to the surface of the eye in attempting to break the greater capillary attraction which keeps the soft contact lens on the eye.

STATEMENT OF PRIOR ART

U.S. Pat. No. 4,079,976 is illustrative of a type of device for placing and removing soft contact lenses. In particular, a tip means 12 is provided to hold lens 16 by force of adhesion for purposes of application of a contact lens on the eye. To remove the lens 16, the user squeezes suction means 52 and aligns tip means 12 with the eye 20 using an optical target 54. The use of suction to lift the contact lens off the eye has the above-identified disadvantages, including the possible injury to the eye. Further, the use of an optical target does not eliminate the possibility of the user improperly placing the tip too close to the eye and causing injury in attempting to put the tip properly on the contact prior to suction being applied.

Other prior art in the general field of soft contact lens removers but not related to this invention are U.S. Pat. Nos. 3,879,076 and 4,082,339.

The present invention removes the contact lens by providing a clamp means which operates to simulate the finger's action in removing soft lenses. The capillary attraction between the lens and eye is broken by the tips of the clamp device which is significantly safer and surer than the above-identified suction type device.

SUMMARY OF THE INVENTION

An object of this invention is to provide a soft contact lens remover which is efficient to use, safe and inexpensive to manufacture.

Another object of the present invention is to provide such a soft contact lens remover which approximates the normal action of the users fingers, while eliminating the requirement of the fingers actually being used to squeeze and pinch the contact lens off the eye.

Another object of this invention is to provide a contact lens remover which may be portable so as to be carried wherever the user goes.

Another object of this invention is to provide a soft contact lens remover which is susceptible to being easily sterilized and stored for instant retrieval and use.

Other objects, advantages and features of this invention will become more apparent from the following description.

In accordance with the principles of this invention, and in achieving the above-identified objects, the present invention provides for a soft contact lens apparatus comprising a clamp device having a general elongated U-shape, with a control portion being defined rearwardly of an intermediate portion, having clamp fingers defined forwardly thereof, with the control portion being squeezed together to open the fingers of the clamp. The fingers terminate in respective tips made of a firm yet soft material.

In order to remove the soft contact lens from the eye, the capillary attraction between the lens and the eye must be broken. This is accomplished with the present invention by providing the tips. The tips are horizontally aligned with respect to the eye, and the control portion is squeezed together opening the tips to a spacing which is slightly greater than the diameter of the lens. The capillary attraction is broken either at the edge of the lens as the control portion is released and the tips move together, or the tips frictionally grab the contact lens while on the eye, and upon complete release of the control portion, the tips squeeze together from the article's natural resiliency pinching the contact lens and breaking capillary attraction so that it can be removed from the eye. It is contemplated that the present invention can be molded and manufactured of a resilient rubber material, with the tip ends being soft enough to prevent damage or injury to the eye or lens, yet firm enough to fold the contact lens off the eye.

The tips which hold the lens may also be used to insert the lens by placing the resilient tips against the cornea to insert the lens.

DETAILED DESCRIPTION

Figure 1:
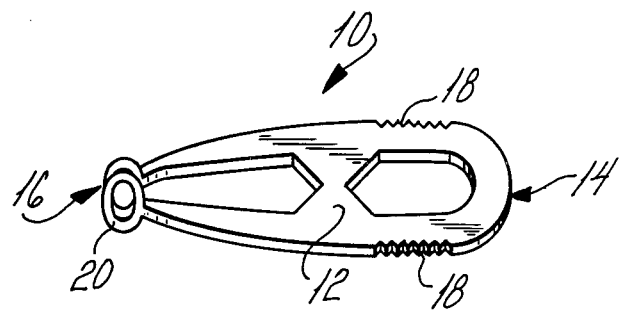
FIG. 1 is a side perspective view of a clamp device of the instant invention illustrated with the clamp fingers close together.
Figure 2:
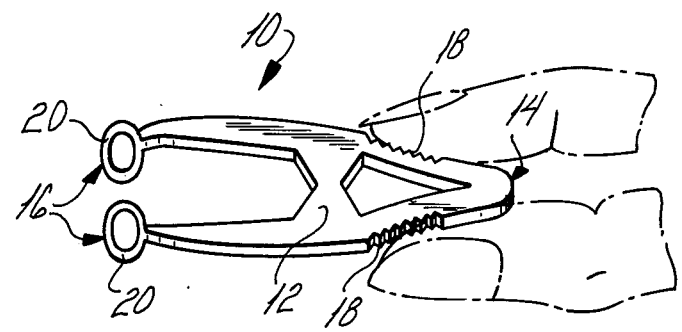
FIG. 2 is a view similar to FIG. 1 with the control portion squeezed together so that the clamp fingers are spread apart.

Referring to the drawings, there is shown in FIG. 1 a contact lens apparatus of this device generally illustrated with the numeral 10 comprising a generally elongated U-shape formed of a resilient material having an intermediate portion 12 with a control portion 14 defined rearwardly of the intermediate portion and clamp fingers 16 defined forwardly thereof. Intermediate portion 12 functions as a fulcrum, so that when control portion 14 is squeezed together, a reverse motion or indirect action is imparted to clamp fingers 16 spreading them apart, as seen in FIG. 2.

The control portion 14 is provided with ribbed finger control sections 18, along the opposite outer edges thereof, while the clamp fingers 16 terminate in tips 20. In the view illustrated in FIG. 1, with the control section in its normal relaxed position, the tips 20 are close together with a slight spacing therebetween.

Figure 3:
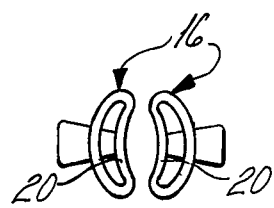
FIG. 3 is a front view illustrating the curvature of the tip extensions of the clamp fingers.

Referring to FIG. 3, there is shown a further detail of the tips which are formed of a generally curved outwardly flared O-shaped ring of a rubbery or resilient type of material, easily deformable to conform to the shape of the eye so as to grab onto the contact lens on the eye. The material chosen for the tips is soft enough to prevent injury or damage to the eye or contact lens, but firm enough to hold on to the soft contact lens as it is being pinched together and it is removed from the surface of the eye.

The clamp is formed of a resilient material, capable of being disinfected. More importantly, the material contains sufficient firmness so as to enable it to be efficiently manipulated, yet is comprised of sufficient softness so as to prevent injury to the eye or lens if the clamp is moved too close to the eye with too sudden a force. The provision of soft tips 20 formed of the above-identified general O-shaped ring is illustrative of a construction which enables a soft yet firm front surface to be provided. The shape of the front surface may be the above-identified curve or any other shape which will generally conform easily to the surface of the eye upon a slight application of pressure between the clamp and the eye while the contact lens is being removed.

The clamp fingers essentially terminate in outwardly flared engaging surfaces which are contoured to the shape of the eye and the shape of the lens. These surfaces are almost lip-like in appearance, and when the lens is placed in these surfaces, it may be placed on the eye by merely placing the lens in the surfaces on the cornea of the eye. Since the material is resilient, it easily conforms to the shape of the eye, thus inserting or depositing the lens thereon.

Referring again to FIG. 2, there is shown the control means 14 squeezed together which causes the corresponding reverse or indirect motion in the contact fingers 16 and tips 20 to spread the tips apart. Preferably, the spread between tips 20 should be no greater than 1 or 2 millimeters more than the diameter of the soft contact lens in order to enable the device to efficiently work.

In actual operation, it is preferred that the contact lens first be removed from the cornea to the sclera by placing the tips 20 in their closed position against the contact lens and moving it off the cornea. While off the cornea, the control portion 14 is squeezed together, thereby opening tips 20. The tips are located horizontally across the eye and break the capillary attraction between the lens and the eye as the control portion is being released. This occurs either by the tips breaking the capillary attraction at the edge of the lens or by grabbing the lens between the fingers and the contact lens is squeezed or pinched together as it is removed from the eye.

The contact lens remover may be made of a unitary assembly or may be made of separate components joined or connected together. Preferably, inexpensive molding material, such as a rubber or rubbery type plastic may be employed to fabricate the contact lens remover.

It should be noted that the contact lens remover of this invention serves as a sterile means of removing the soft contact lens, since the user's fingers do not touch the lens. In some instances, such sterility is important and desirable to prevent contamination, and due to the material used to form the device, it may be stored in a disinfecting solution.

The contact lens remover of this invention is adapted to operate effectively with all sizes of soft contact lenses.

The above-description of this invention illustrates but one preferred embodiment thereof, and other embodiments of the invention as specifically set forth in this application may be achieved without departing from the invention as defined in this patent application.

I claim:

1. A soft contact lens apparatus comprising a clamp having a control portion, an intermediate portion, and clamp fingers, said intermediate portion comprising a fulcrum with said control portion being defined rearwardly of said fulcrum and said clamp fingers being defined forwardly of said fulcrum, said control portion opening said fingers when said control portion is squeezed together, said fingers being opened to no greater than substantially the diameter of a soft contact lens, said clamp fingers terminating forwardly in outwardly flared engaging resilient contoured surfaces with respect to a longitudinal axis of said apparatus, said flared contoured surfaces holding said contact lens, said surfaces moving together pinching said contact lens together as the control portion is released to remove the lens from the eye, said contoured surfaces holding said contact lens.

2. A soft contact lens apparatus as set forth in claim 1, wherein said control portion, intermediate portion and clamp fingers are integrally formed of an unitary member.

3. A soft contact lens apparatus as set forth in claim 1, wherein said clamp comprises a rubbery material.

4. A soft contact lens apparatus as set forth in claim 1, wherein said flared contoured surfaces comprise a rubbery material.

5. A soft contact lens apparatus as set forth in claim 1, wherein said surfaces are separated to a distance of no greater than 18 millimeters when fully opened.

6. A soft contact lens apparatus as set forth in claim 1, wherein said clamp comprises an elongated U-shape with said fingers defined forwardly of said fulcrum and said control portion forming the seat of the U-shape.

7. A soft contact lens remover as set forth in claim 6, wherein said clamp comprises a unitary assembly.

8. A soft contact lens remover as set forth in claim 1, wherein said apparatus comprises a material susceptible to easy disinfection.

9. A soft contact lens apparatus as set forth in claim 1, wherein said surfaces comprise symmetrical contour shapes about said longitudinal axis.

10. A soft contact lens apparatus as set forth in claim 9, wherein said contoured surfaces are formed by tips extending forwardly from said clamp fingers.

11. A soft contact lens apparatus as set forth in claim 10, wherein said tips comprise curved O-ring members.

* * * * *